United States Patent
Kim et al.

(10) Patent No.: US 10,362,996 B2
(45) Date of Patent: Jul. 30, 2019

(54) DEVICE FOR CORRECTING LIGHT ABSORPTION SPECTRUM, METHOD OF MANUFACTURING THE DEVICE, AND METHOD OF CORRECTING LIGHT ABSORPTION SPECTRUM

(71) Applicant: SAMSUNG ELECTRONICS CO., LTD., Suwon-si (KR)

(72) Inventors: Sangkyu Kim, Yongin-si (KR); Joonhyung Lee, Yongin-si (KR); Seongho Cho, Gwacheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 948 days.

(21) Appl. No.: 14/818,485

(22) Filed: Aug. 5, 2015

(65) Prior Publication Data
US 2016/0089088 A1 Mar. 31, 2016

(30) Foreign Application Priority Data
Sep. 29, 2014 (KR) .................. 10-2014-0130326

(51) Int. Cl.
*A61B 5/00* (2006.01)
*G01N 21/23* (2006.01)
(Continued)

(52) U.S. Cl.
CPC .......... *A61B 5/7278* (2013.01); *A61B 5/0075* (2013.01); *A61B 5/6843* (2013.01);
(Continued)

(58) Field of Classification Search
CPC ... A61B 5/7278; A61B 5/0059; A61B 5/7246; A61B 2562/12; G01N 21/35; G01N 2201/1218
See application file for complete search history.

(56) References Cited

U.S. PATENT DOCUMENTS 5,370,114 A * 12/1994 Wong ................. A61B 5/14532
356/39
6,362,144 B1 * 3/2002 Berman ............. A61B 5/14532
510/140
(Continued)

FOREIGN PATENT DOCUMENTS

JP 2006-194800 A 7/2006
JP 4308868 B2 8/2009

*Primary Examiner* — Sang H Nguyen
(74) *Attorney, Agent, or Firm* — Sughrue Mion, PLLC

(57) ABSTRACT

Provided are light absorption spectrum correction devices, methods of manufacturing the light absorption spectrum correction devices, and methods of correcting a light absorption spectrum. The light absorption spectrum correction device includes: a light source configured to emit light; an attenuated total reflectance (ATR) crystal layer configured to contact a subject and provide an optical passage along which the light emitted from the light source travels to the subject; a pressure sensor configured to detect a contact pressure applied to the ATR crystal layer by the subject; a spectrum detector and analyzer configured to detect light emitted from the ATR crystal layer, form a light absorption spectrum based on the detected light, and determine an intensity of the light emitted from the ATR crystal layer; and a spectrum correction device configured to correct the light absorption spectrum based on the contact pressure.

11 Claims, 10 Drawing Sheets

(51) Int. Cl.
  *G01N 21/35* (2014.01)
  *G01N 21/552* (2014.01)
(52) U.S. Cl.
  CPC ........... *A61B 5/7246* (2013.01); *G01N 21/35* (2013.01); *G01N 21/552* (2013.01); *A61B 2562/12* (2013.01); *G01N 2201/1218* (2013.01)

(56) References Cited

U.S. PATENT DOCUMENTS

| | | | |
|---|---|---|---|
| 6,424,851 | B1 | 7/2002 | Berman et al. |
| 7,167,735 | B2 * | 1/2007 | Uchida .............. A61B 5/14532 600/310 |
| 8,970,838 | B2 * | 3/2015 | Messerschmidt ...... G01N 21/65 356/301 |
| 2003/0031597 | A1 * | 2/2003 | Sota .................. A61B 5/14532 422/82.09 |
| 2004/0121358 | A1 * | 6/2004 | Uchida ................ A61B 5/0059 435/6.11 |
| 2005/0056080 | A1 | 3/2005 | Lucci et al. |
| 2005/0137469 | A1 * | 6/2005 | Berman ............. A61B 5/14532 600/316 |
| 2005/0171413 | A1 * | 8/2005 | Blair ................. A61B 5/14532 600/310 |
| 2011/0001965 | A1 * | 1/2011 | Messerschmidt ...... G01N 21/43 356/317 |
| 2015/0338338 | A1 * | 11/2015 | Messerschmidt .... A61B 5/0075 435/288.7 |

* cited by examiner

DEVICE FOR CORRECTING LIGHT ABSORPTION SPECTRUM, METHOD OF MANUFACTURING THE DEVICE, AND METHOD OF CORRECTING LIGHT ABSORPTION SPECTRUM

CROSS-REFERENCE TO RELATED APPLICATION

This application claims priority from Korean Patent Application No. 10-2014-0130326, filed on Sep. 29, 2014 in the Korean Intellectual Property Office, the disclosure of which is incorporated herein in its entirety by reference.

BACKGROUND

1. Field

Apparatuses and methods consistent with exemplary embodiments relate to processing data obtained from a body under examination, and more particularly, to devices for correcting light absorption spectrum of a body under examination, methods of manufacturing the devices, and methods of correcting light absorption spectrums.

2. Description of the Related Art

Attenuated total reflectance (ATR) crystals are used in spectrum analysis using light in an infrared band. The ATR crystals may be utilized for measuring a biosignal in a non-invasive manner.

In order to measure a biosignal in a non-invasive manner, a subject under medical examination may be brought into contact with ATR crystals. At this point, a contact pressure between the ATR crystals and the subject may be variable, and accordingly, the intensity of a light absorption spectrum with respect to the subject may also be variable. In the case of a general bench-top equipment, a light absorption spectrum can be measured by measuring a liquid or by applying a constant pressure to the subject. However, when the subject is a biological body (for example, a human body), it is difficult to maintain a constant contact pressure on the body.

SUMMARY

One or more exemplary embodiments provide spectrum correction devices configured to reduce a variation of light absorption spectrum with a change in a contact pressure with respect to a body under examination.

Further, one or more exemplary embodiments provide methods of manufacturing the spectrum correction devices.

Further still, one or more exemplary embodiments provide methods of correcting a light absorption spectrum by using the spectrum correction devices.

According to an aspect of an exemplary embodiment, there is provided a light absorption spectrum correction device including: a light source configured to emit light; an attenuated total reflectance (ATR) crystal layer configured to contact a subject and provide an optical passage along which the light emitted by the light source travels to the subject; a pressure sensor configured to detect a contact pressure applied to the ATR crystal layer by the subject; a spectrum detector and analyzer configured to detect light emitted from the ATR crystal layer, form a light absorption spectrum based on the detected light, and determine an intensity of the light emitted from the ATR crystal layer; and a spectrum correction device configured to correct the light absorption spectrum based on the contact pressure.

The spectrum detector and analyzer is further configured to form the light absorption spectrum based on an intensity and a wavelength of the detected light.

In the light absorption spectrum correction device, the spectrum correction device may be connected to the pressure sensor and the spectrum detector and analyzer.

The light source, the pressure sensor, and the spectrum detector and analyzer may be provided on a same substrate.

The pressure sensor may be provided on a substrate, and the light source and the spectrum detector and analyzer may be provided above the substrate.

The ATR crystal layer may be disposed on the pressure sensor and in contact with the pressure sensor.

The light absorption spectrum correction device may further include a material layer disposed between the ATR crystal layer and the pressure sensor, wherein the material layer has a refractive index less than that of the ATR crystal layer.

The spectrum correction device may be only connected to the substrate.

The spectrum correction device may include a data-base of contact pressure-light intensities.

The light absorption spectrum correction device may further include a pressure arm configured to apply force to the subject, wherein the contact pressure corresponds to the force applied to the subject.

According to an another aspect of an exemplary embodiment, there is provided a method of manufacturing a light absorption spectrum correction device including: forming an ATR measuring apparatus by disposing a pressure sensor, a light source, an ATR crystal layer, and a spectrum detector and analyzer on a substrate; and connecting a spectrum correction device to the ATR measuring apparatus.

The pressure sensor, the light source, and the spectrum detector and analyzer may be formed on a same plane. In this case, the spectrum correction device may be connected to the substrate only.

The light source and the spectrum detector and analyzer may be formed on a different plane from the pressure sensor. At this point, the spectrum correction device may be connected to the substrate and the spectrum detector and analyzer.

According to an another aspect of an exemplary embodiment, there is provided a method of correcting a light absorption spectrum in a light absorption spectrum correction device including: measuring a contact pressure applied onto the device by a subject; measuring a light absorption spectrum with respect to the body under examination; and correcting the light absorption spectrum based on the measured contact pressure and the light absorption spectrum.

The measuring of the light absorption spectrum may further include: recognizing that an ATR crystal layer is in contact with the subject; radiating light onto the subject through the ATR crystal layer; and detecting light emitted from the ATR crystal layer.

The correcting of the light absorption spectrum may include: obtaining base data from the measured contact pressure and the light absorption spectrum; comparing the base data with a reference region of a graph that indicates a contact pressure-light intensity with respect to the subject; correcting the base data to be within the reference region in response to the base data being outside the reference region; and correcting the light absorption spectrum according to the corrected base data.

BRIEF DESCRIPTION OF THE DRAWINGS

The above and/or other aspects will be more apparent and more readily appreciated from the following description of exemplary embodiments, taken in conjunction with the accompanying drawings, in which.

DETAILED DESCRIPTION

Figure 1:
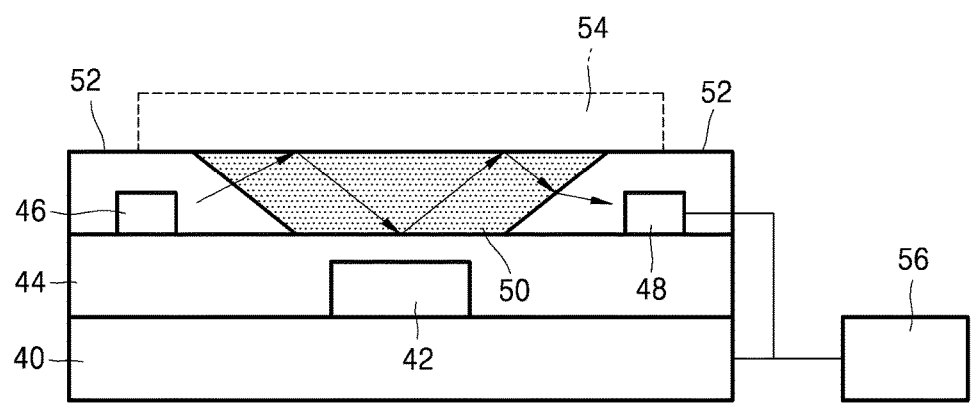
FIG. 1 is a cross-sectional view of a light absorption spectrum correction device according to an exemplary embodiment.

Reference will now be made in detail to exemplary embodiments, examples of which are illustrated in the accompanying drawings, wherein like reference numerals refer to like elements throughout. In the drawings, the thicknesses of layers and regions are exaggerated for clarity.

First, a light absorption spectrum correction device (hereinafter, a correction device) according to an exemplary embodiment will be described.

FIG. 1 is a cross-sectional view of a correction device according to an exemplary embodiment.

As shown in FIG. 1, a pressure sensor 42 is provided on a substrate 40. The substrate 40 may transmit a signal generated from the pressure sensor 42. The substrate 40 may be a substrate on which an element (for example, a wire) for transmitting the signal is formed. The pressure sensor 42 is covered by a first material layer 44. The first material layer 44 has an optical refractive index less than that of an attenuated total reflectance (ATR) crystal layer 50. The first material layer 44 has a flat upper surface. The first material layer 44 may have a certain degree of elasticity. A light source 46 and a spectrum detector and analyzer 48 are formed on the first material layer 44. The light source 46 and the spectrum detector and analyzer 48 are separated from each other. Since light emitted from the light source 46 reaches the spectrum detector and analyzer 48 through the ATR crystal layer 50, the light source 46 and the spectrum detector and analyzer 48 may be disposed in consideration of the light passage. The pressure sensor 42 may be disposed between the light source 46 and the spectrum detector and analyzer 48. The light source 46 and the spectrum detector and analyzer 48 are horizontally separated from the pressure sensor 42. The light source 46 may be a light source generating light of various wavelengths (for example, an infrared ray), but is not limited thereto. The spectrum detector and analyzer 48 detects and analyzes a light absorption spectrum with respect to a subject 54 under examination by detecting light emitting from the ATR crystal layer 50. As a result, a data of light intensity at a specific location (or wavelength) may be obtained from a detected light absorption spectrum. Information obtained in this way is transmitted to a spectrum correction device 56. The subject 54 under examination may be a part of a human subject, for example, a skin, a finger, or a toe.

The ATR crystal layer 50 may be disposed between the light source 46 and the spectrum detector and analyzer 48. A bottom surface of the ATR crystal layer 50 contacts the upper surface of the first material layer 44. Accordingly, a pressure applied to the ATR crystal layer 50 is transmitted to the pressure sensor 42 through the first material layer 44. The surface of the ATR crystal layer 50 that contacts the subject 54 may be at a higher level than the light source 46 and the spectrum detector and analyzer 48. The ATR crystal layer 50 may be fixed in a case 52. The case 52 covers the light source 46 and the spectrum detector and analyzer 48 while fixing the ATR crystal layer 50. The subject 54 may be brought into contact with an outer surface of the ATR crystal layer 50. Light emitted from the light source 46 progresses through the ATR crystal layer 50 while being totally reflected in the ATR crystal layer 50. Therefore, light that enters the ATR crystal layer 50 from the light source 46 may be incident at an angle that causes a total reflection in the ATR crystal layer 50. The condition for total reflection when the subject 54 is on the ATR crystal layer 50 may vary from the condition for total reflection when the subject 54 is not on the ATR crystal layer 50. Accordingly, when the subject 54 is on the ATR crystal layer 50, a portion of the light incident on the upper surface of the ATR crystal layer 50 is reflected and other portion may be absorbed by the subject 54. When a pressure (hereinafter, contact pressure) being applied to the ATR crystal 50 by the subject 54 is changed, properties of light absorbed by the subject 54 change. The properties of the absorbed light may include at least one of intensity, propagation direction, frequency or wavelength spectrum, and polarization. For example, as the contact pressure increases, the amount of energy being absorbed may increase. Also, the degree of light absorption of the subject 54 may vary according to the wavelength of light that is used.

When the contact pressure is applied to the ATR crystal layer 50 by the subject 54, the pressure sensor 42 measures the contact pressure, and the measured contact pressure is transmitted to the spectrum correction device 56.

Figure 2:
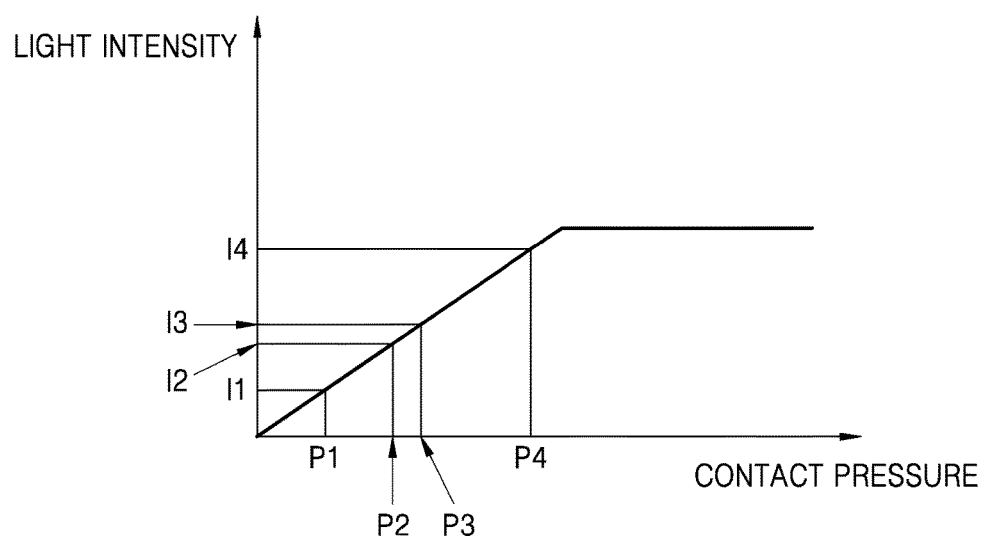
FIG. 2 is a graph showing an example of relationship between a contact pressure and light intensity.

The spectrum correction device 56 is connected to the substrate 40 and the spectrum detector and analyzer 48. Based on data (hereinafter, base data) regarding the contact pressure transmitted from the pressure sensor 42 and the light intensity transmitted from the spectrum detector and analyzer 48, the spectrum correction device 56 confirms whether the transmitted contact pressure and the light intensity are outside of a reference region or not. The confirmation may be achieved through comparison and analysis of the base data with respect to a database of contact pressure-light intensities that is stored in the spectrum correction device 56. The database of contact pressure-light intensities that is stored in the spectrum correction device 56 may be formed from data of light absorption spectrums measured at various contact pressures on the subject 54. A means (for example, a graph or an equation) for expressing the relationship between the contact pressure and the light intensity may be formed from the database of contact pressure-light intensities of the spectrum correction device 56. When the means is a graph as depicted in FIG. 2 and the base data (for example, a contact pressure) is P1 or P4, which is outside of a reference region (for example, P2-P3), the base data is determined as being outside of the reference region. When the base data is a light intensity, it may be determined as the same method as when the base data is the contact pressure.

According to a result of the determination, the contact pressure of the base data is corrected into the range of the reference region, and the light intensity of the base data is also corrected to a light intensity corresponding to the contact pressure that is corrected into the reference region. Through the process of corrections, a light absorption spectrum measured from the subject 54 may be corrected to fit to the corrected light intensity, and the corrected result may be transmitted to a display device to be displayed. The correction of the light absorption spectrum may be performed in the spectrum correction device 56. Hereinafter, devices except the spectrum correction device 56 may be referred to as an ATR measuring apparatus.

Figure 3:
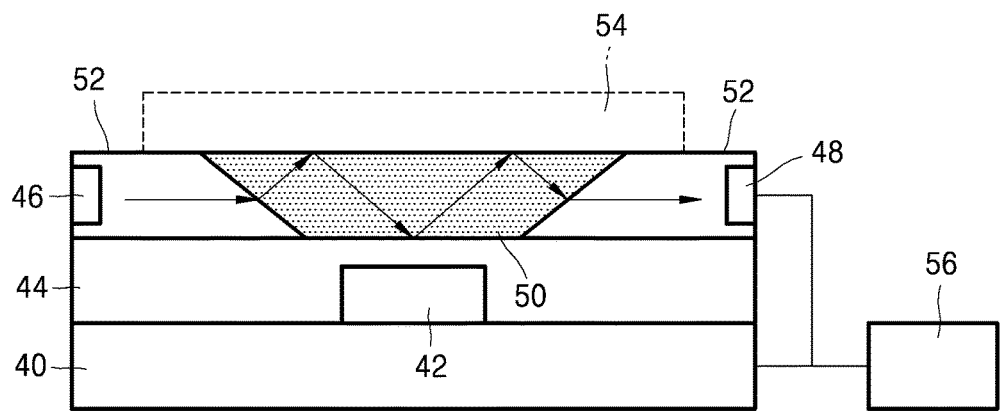
FIG. 3 is a cross-sectional view of a light absorption spectrum correction device according to another exemplary embodimentt.

FIG. 3 is a cross-sectional view of a light absorption spectrum correction device according to another exemplary embodiment. Only constituent elements of the light absorption spectrum correction device of FIG. 3 that are different from those of FIG. 1 will be described below.

As shown in FIG. 3, a light source 46 may be attached to an inner sidewall of a case 52 facing a light incident surface of an ATR crystal layer 50. A spectrum detector and analyzer 48 may be attached to a sidewall of the case 52 facing a light-emitting surface of the ATR crystal layer 50.

Figure 4:
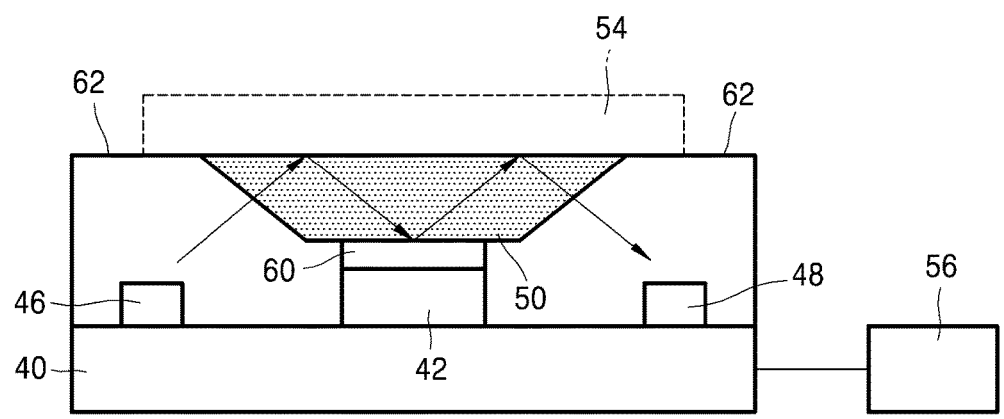
FIG. 4 is a cross-sectional view of a light absorption spectrum correction device according to another exemplary embodiment.

FIG. 4 is a cross-sectional view of a light absorption spectrum correction device according to another exemplary embodiment. Only constituent elements of the light absorption spectrum correction device of FIG. 4 that are different from those of FIG. 1 will be described.

FIG. 4 illustrates a light source 46 and a spectrum detector and analyzer 48 disposed on a substrate 40 together with a pressure sensor 42. The pressure sensor 42 is disposed between the light source 46 and the spectrum detector and analyzer 48. A second material layer 60 is formed on the pressure sensor 42. The second material layer 60 has a refractive index less than that of an ATR crystal layer 50. The second material layer 60 may be formed of the same material as used to form the first material layer 44. The second material layer 60 may cover an entire upper surface of the pressure sensor 42. The ATR crystal layer 50 is formed on the second material layer 60. A bottom surface of the ATR crystal layer 50 contacts the second material layer 60. The ATR crystal layer 50 may be fixed by a case 62. A portion of an upper surface of the ATR crystal layer 50 may contact the case 62. A spectrum correction device 56 may be connected only to a substrate 40 of the ATR measuring apparatus. The spectrum correction device 56 may be connected to the pressure sensor 42 and the spectrum detector and analyzer 48 through the substrate 40. Accordingly, the substrate 40 may include an element (for example, a wire) that connects the spectrum correction device 56 to the spectrum detector and analyzer 48.

Figure 5:
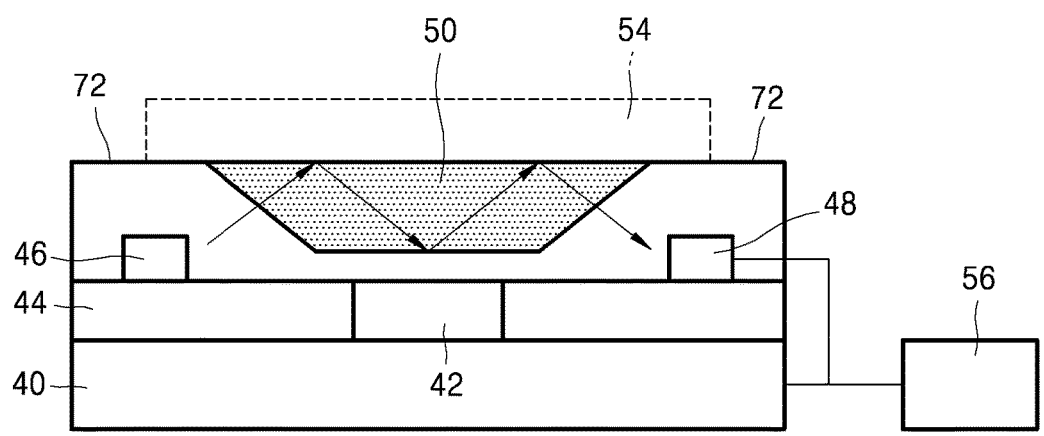
FIG. 5 is a cross-sectional view of a light absorption spectrum correction device according to another exemplary embodiment.

FIG. 5 is a cross-sectional view of a light absorption spectrum correction device according to another exemplary embodiment. Only constituent elements of the light absorption spectrum correction device of FIG. 5 that are different from those of FIG. 1 will be described.

Referring to FIG. 5, a first material layer 44 is formed around a pressure sensor 42. The first material layer 44 may have the same height as the pressure sensor 42. Upper surfaces of the pressure sensor 42 and the first material layer 44 are flat. A case 72 is formed above the first material layer 44. The case 72 may contact the entire upper surface of the first material layer 44 and the entire upper surface of the pressure sensor 42. A light source 46 and a spectrum detector and analyzer 48 are disposed on an inner bottom surface of the case 72. The location relationship of the light source 46 and the spectrum detector and analyzer 48 may be the same as that of the light source 46 and the spectrum detector and analyzer 48 of FIG. 1. The case 72 between the light source 46 and the spectrum detector and analyzer 48 has a concave portion. An ATR crystal layer 50 is mounted on the concaved portion of the case 72. A sloped portion of the concaved portion of the case 72 facing the light source 46 may be an opening-portion for light incident. Also, a sloped portion of the concaved portion of the case 72 facing the spectrum detector and analyzer 48 may be an opening-portion for light emission. A bottom surface of the concaved portion of the case 72 may be parallel to an upper surface of the pressure sensor 42. A height of an upper surface of a circumference of the concaved portion of the case 72 may be at the same level as the upper surface of the ATR crystal layer 50.

In the ATR measuring apparatuses described above, the ATR crystal layer 50 may directly contact the pressure sensor 42. However, at this point, there may be a wearing problem as a result of direct contact.

Figure 6:
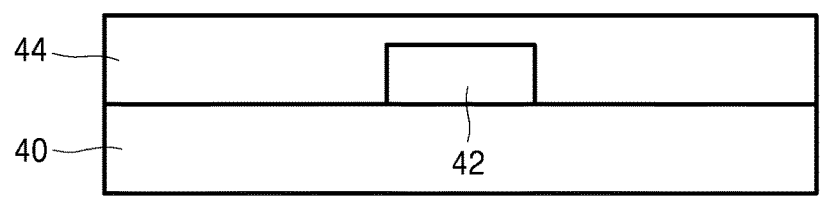
FIGS. 6 through 8 are cross-sectional views for explaining a method of manufacturing a spectrum correction device according to an exemplary embodiment.
Figure 7:
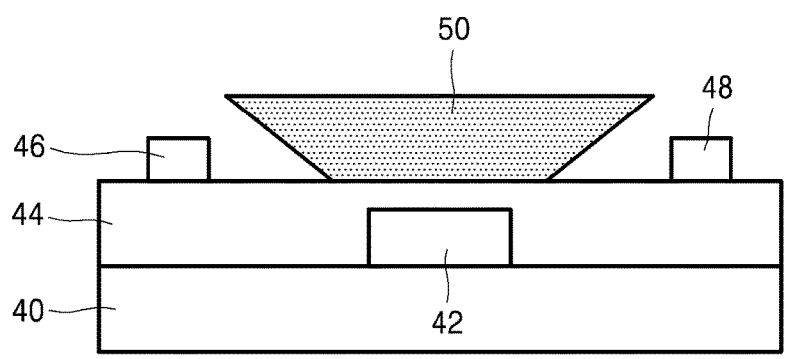
Figure 8:
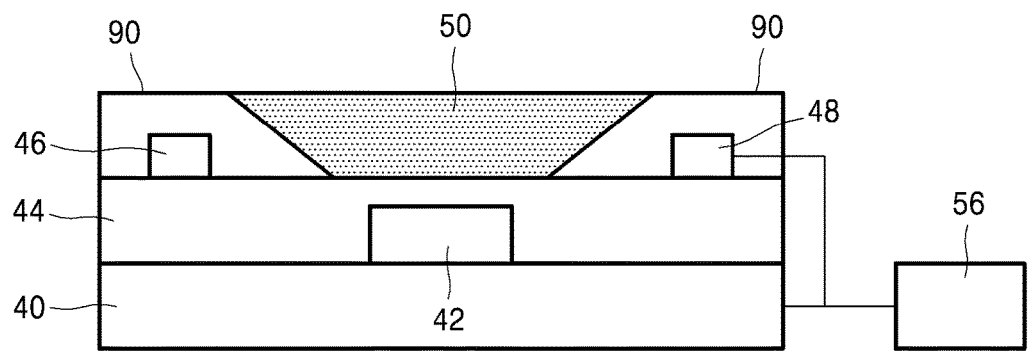

FIGS. 6 through 8 are cross-sectional views for explaining a method of manufacturing a spectrum correction device according to an exemplary embodiment.

Referring to FIG. 6, a pressure sensor 42 is formed or mounted on a substrate 40. After forming a first material layer 44 that covers the pressure sensor 42 on the substrate 40, an upper surface of the first material layer 44 is planarized. The first material layer 44 may have a refractive index less than that of an ATR crystal layer 50 to be formed in a subsequent process.

Referring to FIG. 7, a light source 46 and a spectrum detector and analyzer 48 are formed or disposed on the first material layer 44. The light source 46 and the spectrum detector and analyzer 48 are disposed so that the pressure sensor 42 is located between the light source 46 and the spectrum detector and analyzer 48. The ATR crystal layer 50 is disposed on the first material layer 44 between the light source 46 and the spectrum detector and analyzer 48. The ATR crystal layer 50 is located above the pressure sensor 42. A bottom surface of the ATR crystal layer 50 contacts an upper surface of the first material layer 44. The ATR crystal layer 50 may be attached to the first material layer 44 by using an adhesive. The refractive index of the adhesive may be less than that of the ATR crystal layer 50. The ATR crystal layer 50 is separated from the light source 46. The ATR crystal layer 50 is also separated from the spectrum detector and analyzer 48. The ATR crystal layer 50 may be disposed so that a sloped light incident surface faces the light source 46 and a sloped light emitting surface faces the spectrum detector and analyzer 48.

Referring to FIG. 8, the ATR crystal layer 50 is fixed by a case 90. The light source 46 and the spectrum detector and analyzer 48 are covered by the case 90. Next, the spectrum correction device 56 is connected to the pressure sensor 42 through the substrate 40. The spectrum correction device 56 is also connected to the spectrum detector and analyzer 48. When the spectrum detector and analyzer 48 and the substrate 40 are connected via a connection means, such as a conductive plug, the spectrum correction device 56 may be connected only to the substrate 40.

Next, a method of manufacturing a spectrum correction device according to another exemplary embodiment will be described with reference to FIGS. 9 and 11. Differences from the method described above with reference to FIGS. 6 through 8 will be mainly described hereinafter.

Figure 9:
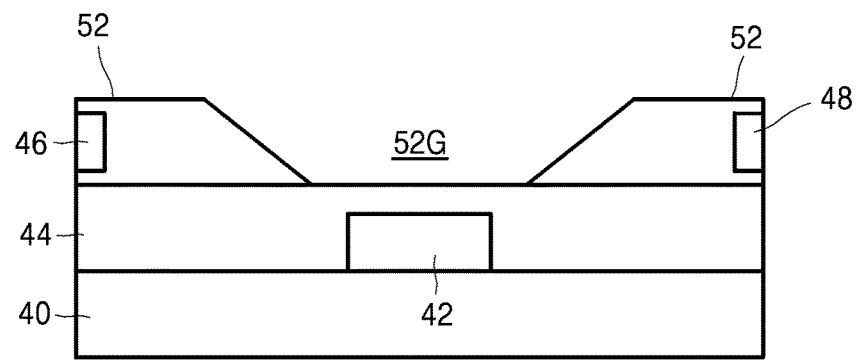
FIGS. 9 and 10 are cross-sectional views for explaining a method of manufacturing a spectrum correction device according to another exemplary embodiment

Referring to FIG. 9, a case 52 is mounted on an upper surface of a first material layer 44 that covers the pressure sensor 42. The case 52 includes a groove 52G onto which an ATR crystal layer 50 will be mounted. The groove 52G is located above the pressure sensor 42. A bottom of the groove 52G is opened and the first material layer 44 is exposed through the bottom of the groove 52G. A light source 46 is mounted on an inner sidewall of the case 52 before mounting the case 52, and a spectrum detector and analyzer 48 may be mounted on the other inner sidewall of the case 52 facing the inner sidewall.

Figure 10:
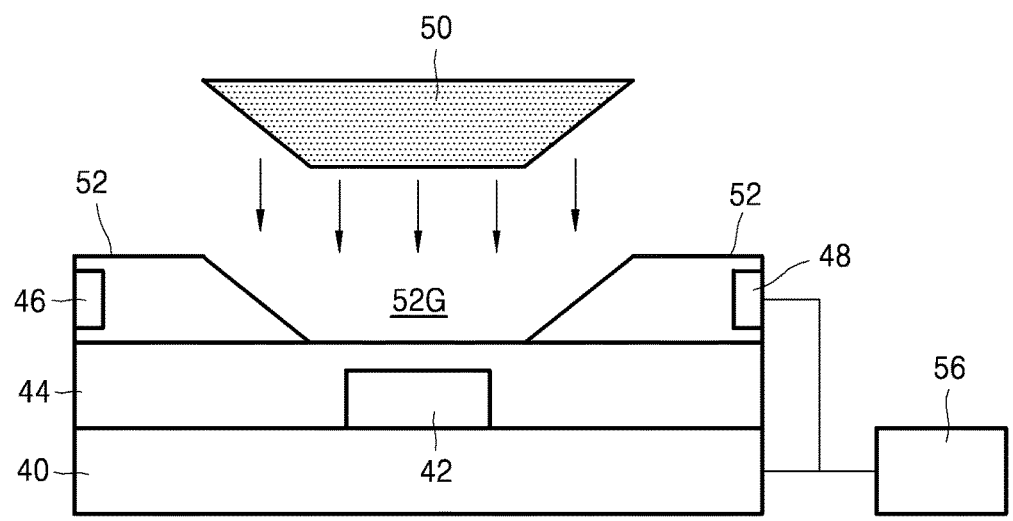

Next, referring to FIG. 10, an ATR crystal layer 50 is mounted on and attached to the groove 52G of the case 52. A bottom surface of the ATR crystal layer 50 is parallel to an upper surface of the first material layer 44. Both side slopes that connect the bottom and upper surfaces of the ATR crystal layer 50 may be parallel to slopes of the groove 52G of the case 52. After mounting the ATR crystal layer 50, a spectrum correction device 56 is connected to remaining elements, that is, the ATR measuring apparatus. The spectrum correction device 56 may also be connected to the substrate 40 and the spectrum detector and analyzer 48.

Figure 11:
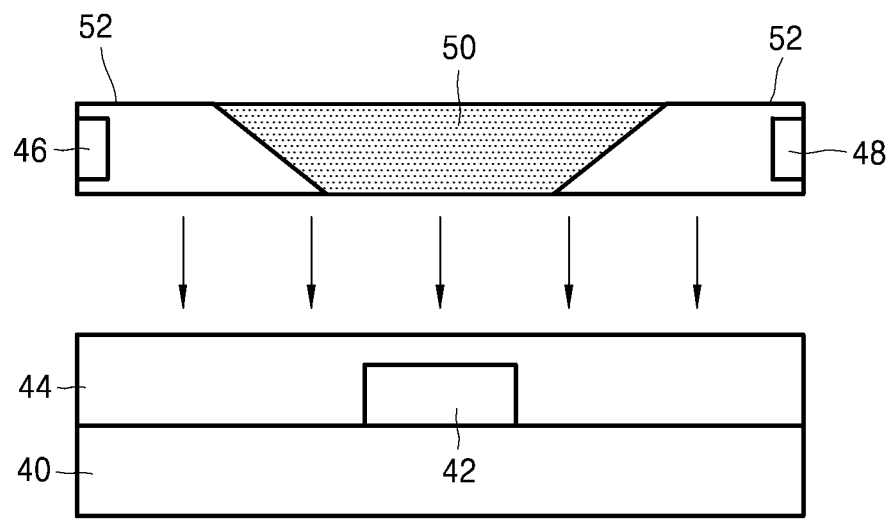
FIG. 11 is a cross-sectional view for explaining another coupling method of an ATR crystal layer in the method of FIG. 10.

As depicted in FIG. 11, a set may be formed by mounting the ATR crystal layer 50 on the case 52 before mounting the case 52 on the first material layer 44, and the set may be mounted or contacted on the upper surface of the first material layer 44.

Another method of manufacturing a spectrum correction device according to another exemplary embodiment will now be described with reference to FIGS. 12 through 16.

Figure 12:
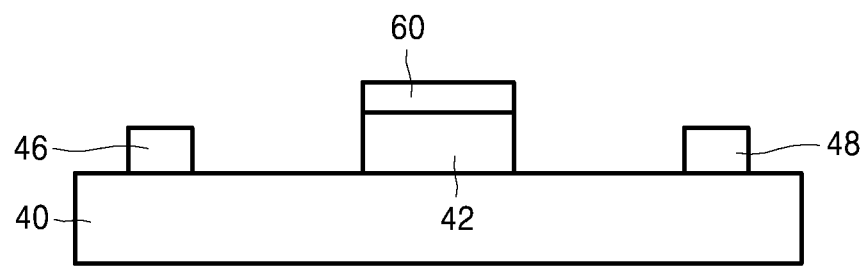
FIGS. 12, 13, 15, and 16 are cross-sectional views for explaining a method of manufacturing a spectrum correction device according to another exemplary embodiment.

Referring to FIG. 12, a light source 46, a pressure sensor 42, and spectrum detector and analyzer 48 are formed or mounted on a substrate 40. The light source 46 and the spectrum detector and analyzer 48 are respectively located on both sides of the pressure sensor 42. The light source 46 and the spectrum detector and analyzer 48 are separated from the pressure sensor 42. A second material layer 60 covers an upper surface of the pressure sensor 42. The pressure sensor 42 may be mounted on the substrate 40 after separately forming the pressure sensor 42. At this point, the pressure sensor 42 may be mounted on the substrate 40 in a state that an upper surface of the pressure sensor 42 is covered by the second material layer 60.

Figure 13:
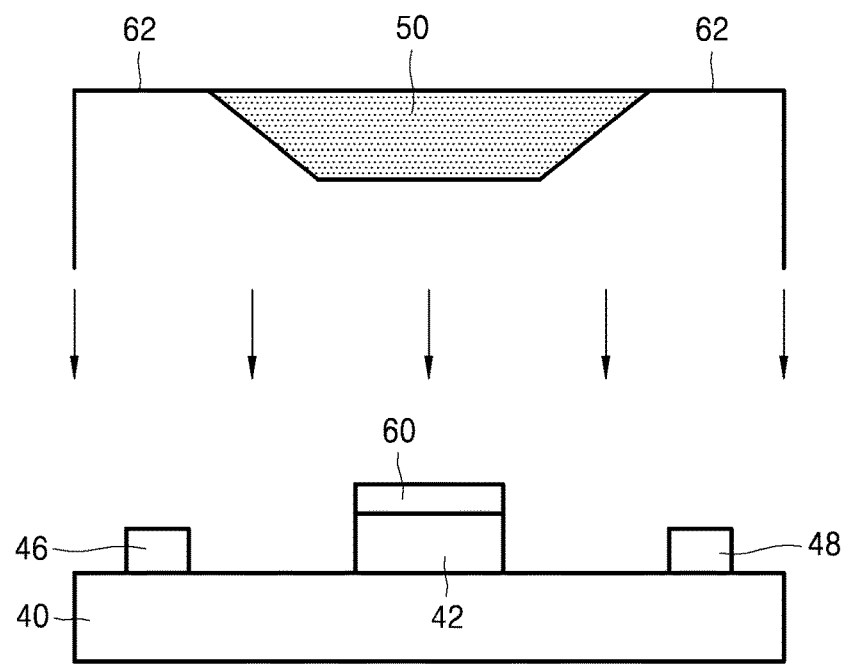
Figure 14:
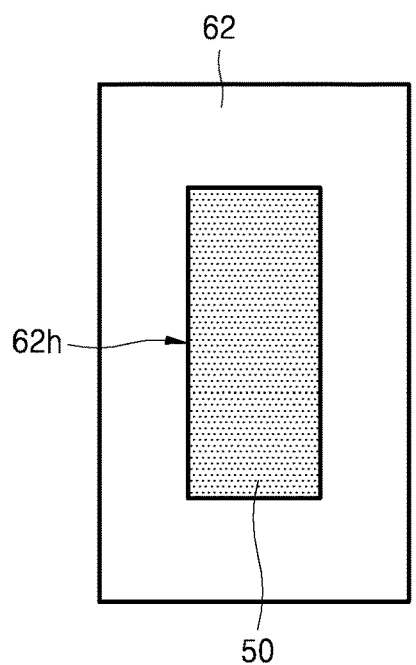
FIG. 14 is a plan view of the spectrum correction device of FIG. 13.

Next, referring to FIG. 13, a case 62 that covers the light source 46, the pressure sensor 42, the second material layer 60, and the spectrum detector and analyzer 48 are aligned on the substrate 40. The ATR crystal layer 50 is attached to an inner ceiling of the case 62. The ATR crystal layer 50 is attached to the inner ceiling of the case 62 through an upper surface of the ATR crystal layer 50. At this point, a portion of the upper surface of the ATR crystal layer 50 (for example, a rim portion) may be attached to the ceiling of the case 62 and the remaining upper surface of the ATR crystal layer 50 may be exposed to the outside. For this purpose, as depicted in FIG. 14, a portion of the case 62 that corresponds to the upper surface of the ATR crystal layer 50 may be opened. That is, a through hole 62h may be formed in the portion of the case 62 to correspond to the upper surface of the ATR crystal layer 50. The majority of the upper surface of the ATR crystal layer 50 may be exposed through the through hole 62h.

Figure 15:
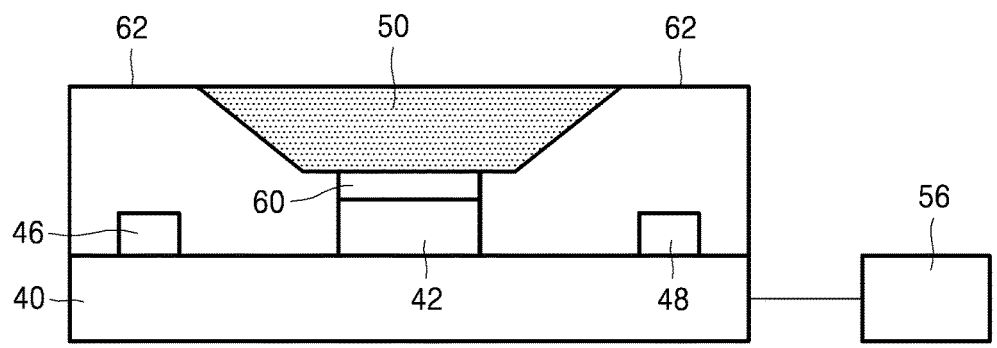

The case 62 on which the ATR crystal layer 50 is then mounted is lowered towards the substrate 40 to mount on or combine with the substrate 40. As depicted in FIG. 15, the case 62 may be mounted on or combined with the substrate 40 so that a bottom surface of the ATR crystal layer 50 contacts the second material layer 60. In this process, without forming the second material layer 60, the bottom surface of the ATR crystal layer 50 may directly contact an upper surface of the pressure sensor 42.

Next, as depicted in FIG. 15, a spectrum correction device 56 is connected to the substrate 40.

Figure 16:
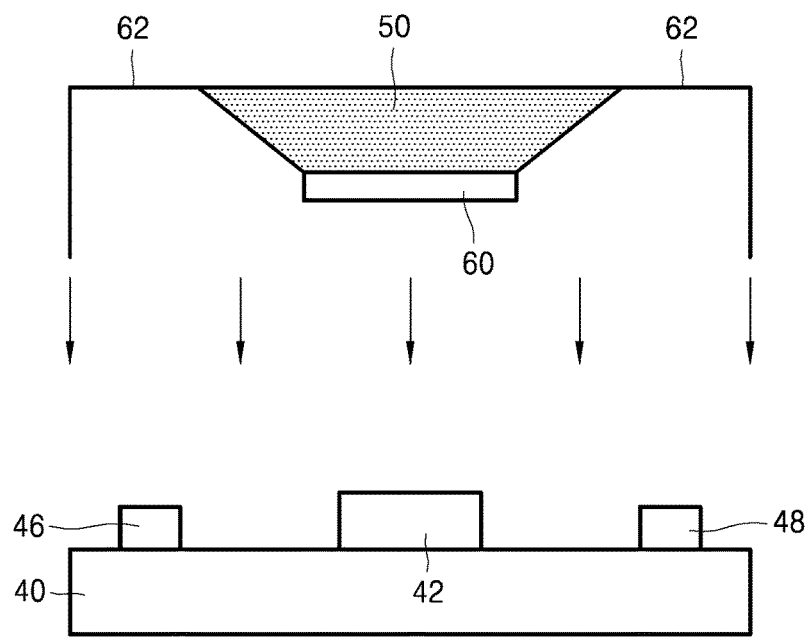

As depicted in FIG. 16, the second material layer 60 may be attached to the bottom surface of the ATR crystal layer 50. In this case, the case 62 is mounted on or combined with the substrate 40 by lowering the case 62 so as to bring the second material layer 60 in contact with the pressure sensor 42.

Alternatively, after mounting the ATR crystal layer 50 on the second material layer 60 that is formed on the upper surface of the pressure sensor 42, the case 62 may be mounted on or combined with the substrate 40 to fix the mounted ATR crystal layer 50.

A method of correcting a spectrum by using a spectrum correction device according to an exemplary embodiment will now be described with reference to FIG. 17 and the spectrum correction device 56 described above.

Figure 17:
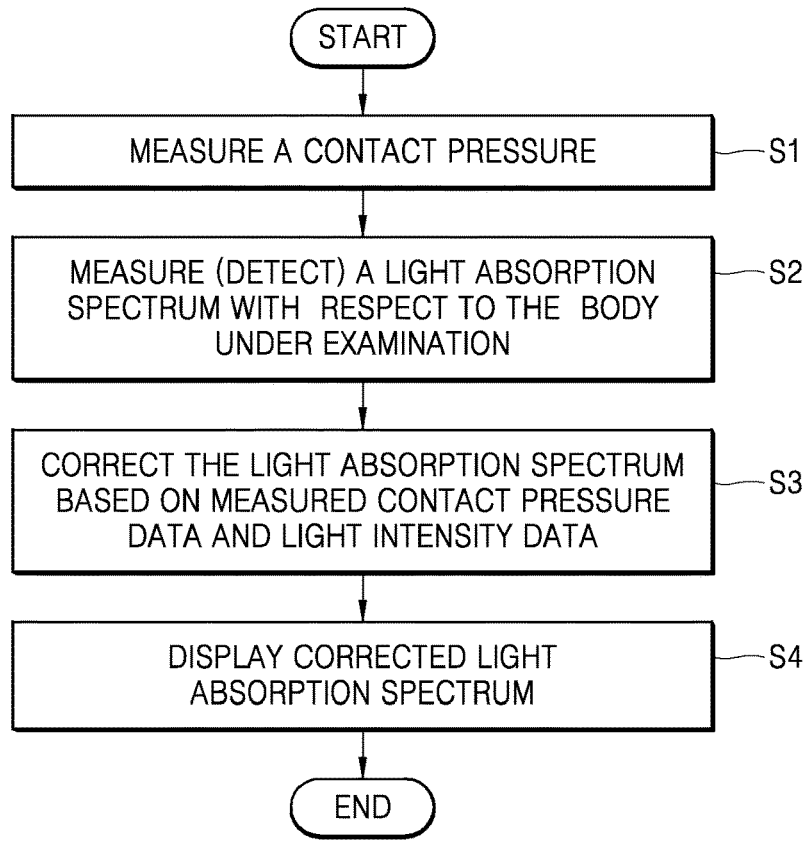
FIG. 17 is a flow-chart for explaining a method of correcting light absorption spectrum according to an exemplary embodiment.

As shown in FIG. 17, first, a contact pressure between the ATR crystal layer 50 and the subject 54 under examination is measured (S1). The contact pressure may be measured by using the pressure sensor 42. A value (data) measured by the pressure sensor 42 may be transmitted to the spectrum correction device 56. Next, a light absorption spectrum with respect to the subject 54 is measured and/or detected (S2). The measurement and/or detection of the light absorption spectrum with respect to the subject 54 may be simultaneously achieved while measuring the contact pressure. The light absorption spectrum with respect to the subject 54 may be formed by detecting light of various wavelengths that are emitted through a light-emitting surface of the ATR crystal layer 50 by using the spectrum detector and analyzer 48. After the light absorption spectrum is formed, information regarding light intensities in a specific wavelength or a specific wavelength band through analysis of the formed light absorption spectrum is obtained. Information obtained in this way may be transmitted to the spectrum correction device 56. A spectrum correction is performed by using the data of contact pressure and light intensities that are transmitted to the spectrum correction device 56 (S3). As described above, the spectrum correction may be achieved by comparing a graph that is formed from the database of contact pressure-light intensities stored in the spectrum correction device 56 and the base data (data regarding the contact pressure and light intensities) transmitted to the spectrum correction device 56. The corrected light absorption spectrum may be displayed to a user through a display device (S4).

An example of correcting a light absorption spectrum will be described with reference to FIGS. 18 through 20.

Figure 18:
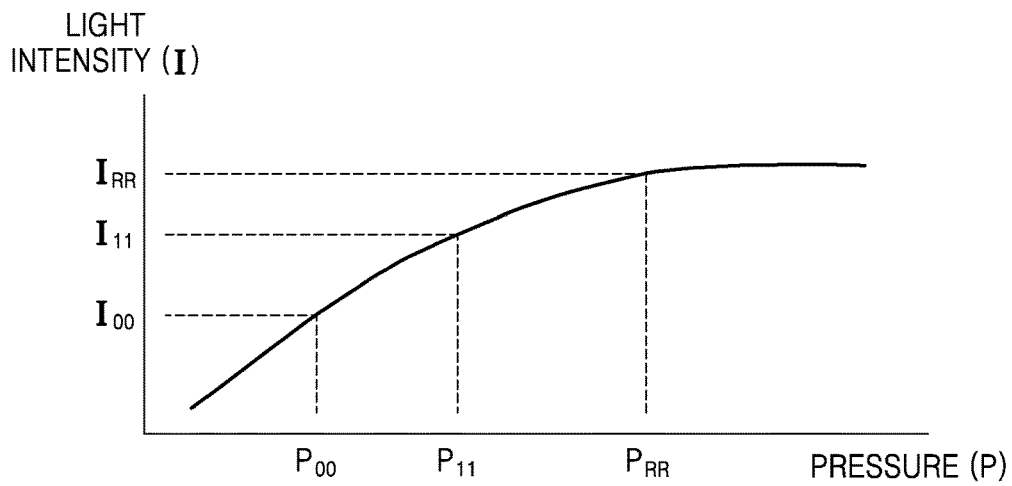
FIGS. 18, 19 and 20 are graphs showing methods of correcting a light absorption spectrum.

FIG. 18 shows a contact pressure-light intensity correction curve, which is stored in an element (for example, the spectrum correction device 56), when a wavelength of incident light is $\lambda_0$.

As shown in FIG. 18, when contact pressures are $P_{00}$, $P_{11}$, and $P_{RR}$, light intensities of spectrums are respectively $I_{00}$, $I_{11}$, and $I_{RR}$. $P_{RR}$ is a reference contact pressure and $I_{RR}$ is a light intensity at $P_{RR}$. Accordingly, when the wavelength of light used is $\lambda_0$ and the contact pressures are $P_{00}$ and $P_{11}$, the measured light intensity (the absorption spectrum) may be corrected to the light intensity $I_{RR}$ when the reference contact pressure is $P_{RR}$ along the curve of FIG. 18.

Figure 19:
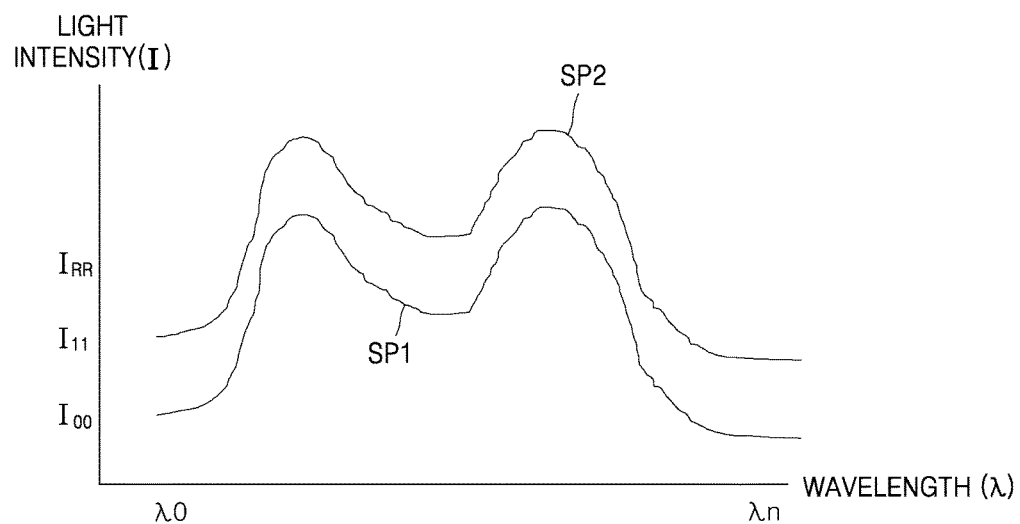
Figure 20:
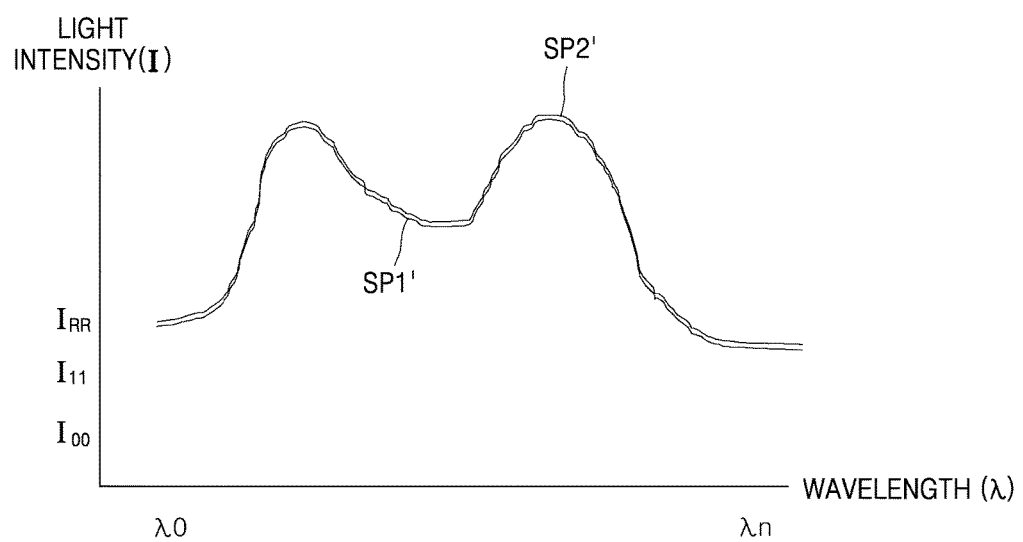

For example, as depicted in FIG. 19, a first spectrum measured at various wavelengths when the contact pressure is $P_{00}$ is SP1 and a second spectrum measured at various wavelengths when the contact pressure is $P_{11}$ is SP2, the correction of the first and second spectrums SP1 and SP2 may be performed as follows.

First, at a wavelength $\lambda_0$, the light intensities $I_{00}$ and $I_{11}$ of the first and second spectrums SP1 and SP2 are corrected to the light intensity $I_{RR}$ when the reference contact pressure is $P_{RR}$. At this point, if the amounts of correction of the light intensities $I_{00}$ and $I_{11}$ of the first and second spectrums SP1 and SP2 are $\Delta I1$ and $\Delta I2$ respectively, light intensities at remaining wavelengths of the first and second spectrums SP1 and SP2 are also corrected by the same correction amounts $\Delta I1$ and $\Delta I2$. As a result, the first and second spectrums SP1 and SP2 may be corrected as depicted in FIG. 20. In FIG. 20, SP1' and SP2' respectively represent the first and second spectrums SP1 and SP2 after corrections.

According to at least one of the above-described exemplary embodiments, the variation of a light absorption spectrum according to a contact pressure on a subject under examination is corrected (a strong light intensity is corrected to a weak light intensity, and a weak light intensity is corrected to a strong light intensity). Accordingly, although a contact pressure on the subject is outside a desired range, the light absorption spectrum may be displayed within a reference region.

While one or more exemplary embodiments have been described with reference to the figures, it will be understood by those of ordinary skill in the art that various changes in form and details may be made therein without departing from the spirit and scope as defined by the following claims.

What is claimed is:

1. A light absorption spectrum correction device comprising:
    a light source configured to emit light;
    an attenuated total reflectance (ATR) crystal layer configured to contact a subject and provide an optical passage along which the light emitted by the light source travels to the subject;
    a pressure sensor configured to detect a contact pressure applied to the ATR crystal layer by the subject;
    a spectrum detector and analyzer configured to detect light emitted from the ATR crystal layer, form a light absorption spectrum based on the detected light, and determine an intensity of the light emitted from the ATR crystal layer;
    a spectrum correction device configured to correct the light absorption spectrum based on the contact pressure; and
    a material layer disposed between the ATR crystal layer and the pressure sensor,
    wherein a refractive index of the material layer is less than a refractive index of the ATR crystal layer.

2. The light absorption spectrum correction device of claim 1, wherein the spectrum detector and analyzer is further configured to form the light absorption spectrum based on an intensity and a wavelength of the detected light.

3. The light absorption spectrum correction device of claim 1, wherein the spectrum correction device is connected to the pressure sensor and the spectrum detector and analyzer.

4. The light absorption spectrum correction device of claim 1, wherein the light source, the pressure sensor, and the spectrum detector and analyzer are provided on a same substrate.

5. The light absorption spectrum correction device of claim 4, wherein the spectrum correction device is only connected to the substrate.

6. The light absorption spectrum correction device of claim 1, wherein the pressure sensor is provided on a substrate, and the light source and the spectrum detector and analyzer are provided above the substrate.

7. The light absorption spectrum correction device of claim 1, wherein the ATR crystal layer is disposed on the pressure sensor and in contact with the pressure sensor.

8. The light absorption spectrum correction device of claim 1, wherein the spectrum correction device comprises a database of contact pressure-light intensities.

9. A method of correcting a light absorption spectrum in a light absorption spectrum correction device, the method comprising:
    measuring, by a pressure sensor, a contact pressure applied onto an attenuated total reflectance (ATR) crystal layer of the light absorption spectrum correction device when the ATR crystal layer is in contact with subject;
    measuring a light absorption spectrum with respect to the subject;
    obtaining base data from the measured contact pressure and the light absorption spectrum;
    determining that the base data is outside a reference region of a graph that indicates a relationship between reference contact pressure values and reference light intensity values, in response to the measured contact pressure being lower than a lowest reference contact pressure value in the reference region of the graph or higher than a highest reference contract pressure value in the reference region of the graph;
    correcting the base data to be within the reference region in response to the base data being outside the reference region; and
    correcting the light absorption spectrum based on the corrected base data.

10. The method of claim 9, wherein the measuring of the light absorption spectrum comprises:
    recognizing that the ATR crystal layer is in contact with the subject;
    radiating light onto the subject through the ATR crystal layer; and
    detecting light emitted from the ATR crystal layer.

11. A light absorption spectrum correction device comprising:
    a light source configured to emit light;
    an attenuated total reflectance (ATR) crystal layer configured to contact a subject and provide an optical passage along which the light emitted by the light source travels to the subject;
    a pressure sensor configured to detect a contact pressure applied to the ATR crystal layer by the subject;
    a spectrum detector and analyzer configured to detect light emitted from the ATR crystal layer, form a light absorption spectrum based on the detected light, and determine an intensity of the light emitted from the ATR crystal layer;

a spectrum correction device configured to correct the light absorption spectrum based on the contact pressure; and a material layer disposed around and the pressure sensor, wherein a height of the material layer is equal to a height of the pressure sensor, and a refractive index of the material layer is less than a refractive index of the ATR crystal layer.

* * * * *